(12) United States Patent
Cao et al.

(10) Patent No.: US 7,772,335 B1
(45) Date of Patent: Aug. 10, 2010

(54) LIGHT OLEFIN SELECTIVE OXYGENATE CONVERSION PROCESS USING CHA FRAMEWORK TYPE ALUMINOSILICATE

(75) Inventors: Guang Cao, Princeton, NJ (US); John F. Brody, Bound Brook, NJ (US); Matu J. Shah, Hackettstown, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 12/412,788

(22) Filed: Mar. 27, 2009

(51) Int. Cl.
*C08F 2/00* (2006.01)
*C07C 1/20* (2006.01)
*C08F 10/02* (2006.01)

(52) U.S. Cl. .................. 526/75; 585/327; 585/638; 585/639

(58) Field of Classification Search ............... 526/75; 585/327, 638, 639
See application file for complete search history.

(56) References Cited

U.S. PATENT DOCUMENTS

| | | | |
|---|---|---|---|
| 4,544,538 A | 10/1985 | Zones | |
| 5,095,163 A | 3/1992 | Barger | |
| 5,958,370 A | 9/1999 | Zones et al. | |
| 6,709,644 B2 | 3/2004 | Zones et al. | |
| 7,067,108 B2 * | 6/2006 | Mertens et al. | 423/709 |
| 7,253,331 B2 * | 8/2007 | Martens et al. | 585/640 |
| 2003/0176751 A1 | 9/2003 | Strohmaier et al. | |
| 2005/0154244 A1 | 7/2005 | Cao et al. | |
| 2005/0197519 A1 | 9/2005 | Cao et al. | |

FOREIGN PATENT DOCUMENTS

WO   WO 03/020641   3/2003

OTHER PUBLICATIONS

Wagner, P. et al., Guest/Host Relationships in the Synthesis of the Novel Cage-Based Zeolites SSZ-35, SSZ-36 and SSZ-39, J. Am. Chem. Soc., 2000, vol. 122, pp. 263-273.

* cited by examiner

*Primary Examiner*—Fred M Teskin
(74) *Attorney, Agent, or Firm*—Kevin M. Faulkner; David M. Weisberg

(57) ABSTRACT

The invention relates to a method for converting an oxygenated hydrocarbon feedstock into an olefin product comprising: (a) forming a CHA framework type aluminosilicate sieve catalyst made from a substantially fluoride-free synthesis mixture comprising silicon and aluminum sources, a slurry medium, and a template, wherein the sieve is substantially free from framework phosphorus and exhibits a Si/Al ratio from about 40-60; (b) optionally formulating the molecular sieve catalyst with an oxidized aluminum-containing precursor matrix material and a clay binder to form a molecular sieve catalyst composition; (c) activating the catalyst by removing/decomposing the template; and (d) contacting the activated catalyst with the feedstock under conditions sufficient to form an olefin product comprising ≧about 65% by weight, on a water-free basis, of ethylene and propylene and having an ethylene-to-propylene ratio ≧about 1.2. Ethylene- and propylene-containing polymers can be formed from the olefin product.

11 Claims, 4 Drawing Sheets

Si/Al = 12.5

Si/Al = 24.0

Si/Al = 46.3

Si/Al = 70.6

Si/Al = 85.1

Si/Al = 85.1

LIGHT OLEFIN SELECTIVE OXYGENATE CONVERSION PROCESS USING CHA FRAMEWORK TYPE ALUMINOSILICATE

FIELD OF INVENTION

This invention relates to methods of converting oxygenates to olefins using CHA framework type aluminosilicates having an intermediate Si/Al ratio that are made using a substantially fluoride-free preparation.

BACKGROUND OF INVENTION

The conversion of oxygenates to olefins (OTO) is currently the subject of intense research because it has the potential for replacing the long-standing steam cracking technology that is today the industry-standard for producing world scale quantities of ethylene and propylene. The very large volumes involved suggest that substantial economic incentives exist for alternate technologies that can deliver high throughputs of light olefins in a cost efficient manner. Whereas steam cracking relies on non-selective thermal reactions of naphtha range hydrocarbons at very high temperatures, OTO exploits catalytic and micro-architectural properties of acidic molecular sieves under milder temperature conditions to produce high yields of ethylene and propylene from methanol.

Current understanding of the OTO reactions suggests a complex sequence in which three major steps can be identified: (1) an induction period leading to the formation of an active carbon pool (alkyl-aromatics), (2) alkylation-dealkylation reactions of these active intermediates leading to products, and (3) a gradual build-up of condensed ring aromatics (coke or coke-like molecules). OTO is therefore an inherently transient chemical transformation in which the catalyst is in a continuous state of change. The ability of the catalyst to maintain high olefin yields for prolonged periods of time relies on a delicate balance between the relative rates at which the above processes take place. The formation of coke-like molecules is of singular importance because their accumulation interferes with the desired reaction sequence in a number of ways. In particular, coke renders the carbon pool inactive, lowers the rates of diffusion of reactants and products, increases the potential for undesired secondary reactions and limits catalyst life.

Over the last several decades, many catalytic materials have been identified as being useful for carrying out the OTO reactions. Crystalline molecular sieves are the preferred catalysts today because they simultaneously address the acidity and morphological requirements for the reactions. Particularly preferred materials are eight-membered ring aluminosilicates, such as those having the chabazite (CHA) framework type, as well as silicoaluminophosphates of the CHA structure, such as SAPO-34. These molecular sieves have cages that are sufficiently large to accommodate aromatic intermediates while still allowing the diffusional transport of reactants and products into and out of the crystals through regularly interconnected window apertures. By complementing such morphological characteristics with appropriate levels of acid strength and acid density, working catalysts are produced. Extensive research in this area indicates that silicoaluminophosphates are currently more effective OTO catalysts than aluminosilicates. In particular, the control of the silica to alumina molar ratio is a key requirement for the use of aluminosilicates in OTO reactions. Nevertheless, aluminosilicate zeolites continue to be explored for use in OTO and appear to have yet undiscovered potential.

Molecular sieves are classified by the Structure Commission of the International Zeolite Association according to the rules of the IUPAC Commission on Zeolite Nomenclature. According to this classification, framework-type zeolites and other crystalline microporous molecular sieves, for which a structure has been established, are assigned a three letter code and are described in the *Atlas of Zeolite Framework Types,* 5th edition, Elsevier, London, England (2001).

One known molecular sieve for which a structure has been established is the material designated as AEI, which is a molecular sieve having pores defined by two sets of generally perpendicular channels each having a cross-sectional dimension about 3.8 Angstrom. Molecular sieves of the AEI framework type do not exist in nature, but a number of aluminophosphates and silicoaluminophosphates having the AEI framework type have been synthesized, including SAPO-18, ALPO-18 and RUW-18. Moreover, because of their small pore size, AEI-type molecular sieves have been reported as suitable catalysts for a variety of important chemical processes, including the conversion of oxygenates to olefins. See, for example, U.S. Pat. No. 5,095,163, incorporated herein by reference.

U.S. Pat. No. 5,958,370, incorporated herein by reference, discloses an aluminosilicate zeolite designated SSZ-39 and having a silica to alumina molar ratio greater than 10, such as 10 to 100. SSZ-39 is produced by crystallizing an aqueous mixture comprising active sources of a trivalent element, such as aluminum, and a tetravalent element, such as silicon, in the presence of certain cyclic or polycyclic quaternary ammonium cations, such as N,N-dimethyl-2,6-dimethylpiperidinium cations, as templating agents. The synthesis can be conducted in the presence of SSZ-39 seed crystals, and there is no disclosure of the presence or absence of fluoride ions in the synthesis mixture.

The highest silica to alumina ratio exemplified for SSZ-39 in U.S. Pat. No. 5,958,370 is a ratio of 51. In column 5, lines 56 to 61, the patent teaches that SSZ-39 can be synthesized directly only as an aluminosilicate, although it suggests that the silica to alumina mole ratio can be increased, potentially to produce an essentially aluminum-free material, by use of standard acid leaching or chelating treatments. However, as is shown in the Comparative Example 13 below, attempts to dealuminize SSZ-39 by acid leaching or chelation have met with only limited success and have failed to produce materials having a silica to alumina ratio greater than 100.

In an article entitled "Guest/Host Relationships in the Synthesis of the Novel Cage-Based Zeolites SSZ-35, SSZ-36 and SSZ-39", J. Am. Chem. Soc., 2000, 122, pages 263-273 Zones and certain of the co-inventors from U.S. Pat. No. 5,958,370 discuss the synthesis and structure of the molecular sieves, SSZ-35, SSZ-36 and SSZ-39. According to this article SSZ-39 is isomorphous with the AEI framework type aluminophosphate molecular sieve SAPO-18 and is a frequently observed product of high-alumina containing syntheses using cyclic and polycyclic quaternized amine structure directing agents. In particular, the article reports that, although SSZ-39 is produced at silica to alumina mole ratios of 30 with a variety of directing agents, including N,N-dimethyl-2,6-dimethylpiperidinium compounds, when the silica to alumina mole ratio is increased to 40 or higher, other crystalline phases, such as SSZ-35 and MFI and MTW framework type materials, are produced.

Chabazite-based zeolites have also been made, some even using preparations that do not contain fluoride, but these reported materials generally have relatively low Si/Al ratios. For instance, U.S. Pat. No. 4,544,538 discloses the synthesis details of SSZ-13, which was experimentally made only at Si/Al ratios as low as 15, with a fluoride-free preparation. Additionally, U.S. Pat. No. 6,709,644 and International Publication No. WO 03/1020641 A1 both disclose the synthesis details of SSZ-62, though, because of the relatively low Si/Al ratios, these disclosures tend to concentrate on aspects of crystal size so as to attain product having less than 0.5 micron particle size.

The present invention relates to methods for converting oxygenates to olefins using aluminosilicates having a CHA framework type, having an intermediate Si/Al ratio, and that are made using a substantially fluoride-free preparation.

SUMMARY

One aspect of the invention relates to a method for converting an oxygenated hydrocarbon feedstock into an olefin product comprising: (a) forming an aluminosilicate molecular sieve catalyst having a CHA framework type, which is made from a synthesis mixture comprising a silicon source, an aluminum source, a slurry medium, and a structure directing agent (template), wherein the synthesis mixture is substantially free from fluorine atoms, and wherein the molecular sieve is substantially free from framework phosphorus and exhibits a Si/Al ratio from about 40 to about 60; (b) optionally formulating the molecular sieve catalyst with an oxidized aluminum-containing precursor matrix material and a clay binder to form a molecular sieve catalyst composition; (c) activating the molecular sieve catalyst by removing and/or decomposing the structure directing agent; and (d) contacting the activated molecular sieve catalyst with an oxygenated hydrocarbon feedstock under conditions sufficient to form an olefin product comprising ethylene and propylene in a combined amount of at least about 65% by weight of the olefin product, on a water-free basis, and wherein the olefin product has an ethylene-to-propylene ratio of at least about 1.2.

Advantageously, the molecular sieve made according to this method can exhibit an x-ray diffraction pattern having at least the following peaks in Table 1:

TABLE 1

| 2Θ (degrees) | Relative Intensities (100 I/Io) |
|---|---|
| 9.44-9.84 | 80-100 |
| 12.89-13.28 | 20-60 |
| 13.97-14.38 | 0-10 |
| 16.07-16.46 | 5-40 |
| 17.83-18.23 | 5-50 |
| 19.15-19.53 | 0-10 |
| 20.73-21.13 | 20-60 |
| 22.54-22.95 | 0-10 |
| 23.20-23.63 | 0-10 |
| 25.13-25.49 | 5-40 |
| 26.10-26.50 | 5-40 |
| 28.39-28.76 | 0-10 |
| 30.92-31.32 | 5-50 |
| 31.35-31.75 | 5-40 |
| 33.78-34.18 | 0-10 |
| 34.87-35.27 | 0-10 |
| 36.37-36.78 | 0-10 |
| 40.14-40.53 | 0-10 |
| 43.28-43.68 | 0-10 |
| 43.92-44.33 | 0-10 |
| 48.27-48.66 | 0-10 |
| 49.42-49.82 | 0-10 |

Also advantageously, the molecular sieve catalyst composition can comprise from about 20% to about 60% (e.g., from more than 40% to about 60%) by weight of the molecular sieve catalyst, and the molecular sieve, the molecular sieve composition, or both can have an attrition resistance index not greater than about 1.5 wt %/hr (e.g., not greater than about 1.0 wt %/hr, not greater than about 0.8 wt %/hr, not greater than about 0.7 wt %/hr, not greater than about 0.6 wt %/hr, or not greater than about 0.5 wt %/hr).

Another aspect of the invention relates to a process for forming an ethylene- and/or propylene-containing polymer comprising: (a) converting an oxygenated hydrocarbon feedstock into an olefin product comprising ethylene, propylene, or both, according to the method of the previous aspect of the invention; (b) separating ethylene, propylene, or both from the olefin product, such that the separated ethylene and/or propylene comprises sufficiently low content(s) of conversion by-products so as to enable polymerization of the separated ethylene and/or propylene; and (c) optionally in the presence of a polymerization catalyst, and optionally in combination with one or more other comonomers and/or a diluent, polymerizing the separated ethylene and/or propylene under conditions sufficient to form an ethylene- and/or propylene-containing homopolymer, copolymer, or combination thereof.

BRIEF DESCRIPTION OF THE DRAWINGS

FIG. 5 shows a temperature-dependent x-ray diffraction pattern for an aluminosilicate CHA framework-type material having an Si/Al ratio of about 85.8, while

DETAILED DESCRIPTION OF THE PREFERRED EMBODIMENTS

Figure 1:
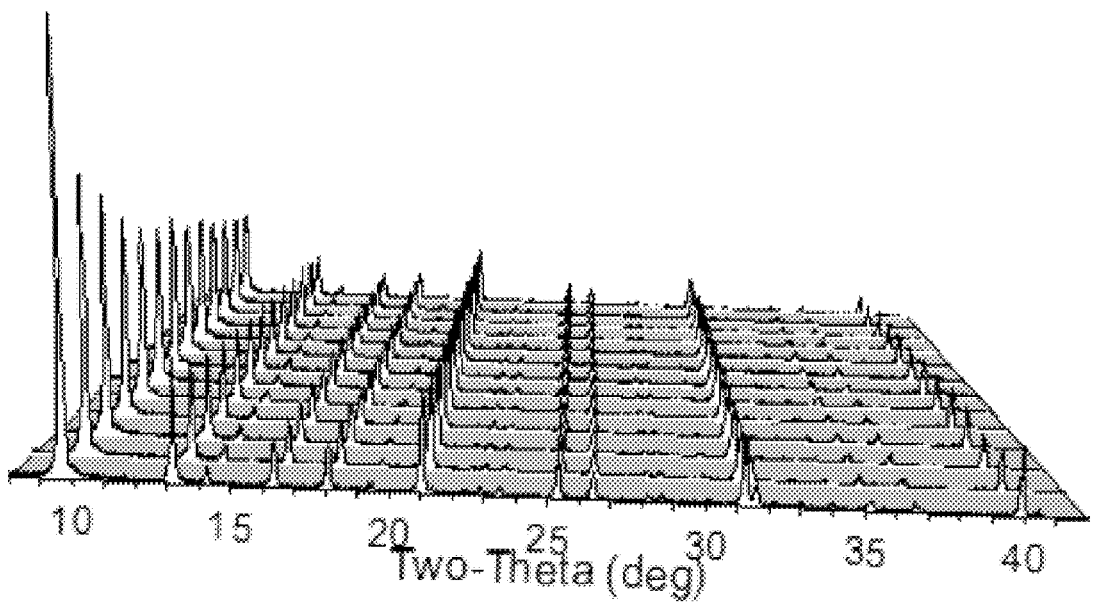
FIG. 1 shows a temperature-dependent x-ray diffraction pattern for an aluminosilicate CHA framework-type material having an Si/Al ratio of about 12.5.

The present invention relates to methods for converting oxygenates, particularly containing methanol and/or dimethylether, to olefins, particularly ethylene and/or propylene, using aluminosilicates having a CHA framework type, having an intermediate Si/Al ratio (e.g., from about 40 to about 60), and that are made using a substantially fluoride-free preparation. A substantially fluoride-free preparation can be sought for many reasons, including but not limited to the following: fluoride ions present in sieve formation do not generally get incorporated into the framework structure but instead are driven off during sieve calcination, usually in the form of HF, which can pose significant health, safety, and environmental (disposal) issues; and fluoride ions can also cause corrosion of certain metal surfaces, e.g., those of an autoclave/calcination chamber.

As used herein, the phrase "substantially fluoride-free," in reference to a preparation of a molecular sieve (crystalline) material, should be understood to mean that no component is added to the reaction mixture that contains more than 1.0 mol % fluorine atoms (e.g., no more than 0.5 mol % fluorine atoms, no more than 0.2 mol % fluorine atoms, no more than 0.1 mol % fluorine atoms), based on the moles of atoms in the particular component. In addition, "substantially fluoride-free," as used herein, is synonymous with "substantially free of fluorine atoms" and should be understood to mean that, regardless of the components added to the reaction mixture, the preparation itself contains no more than 0.2 mol % fluorine atoms (e.g., no more than 0.1 mol % fluorine atoms, no more than 0.05 mol % fluorine atoms, or no more than 0.01 mol % fluorine atoms), based on the moles of atoms in the entire preparation. In a preferred embodiment, the molecular sieve material is completely fluoride free, i.e., contains 0 mol % fluorine atoms.

Also as used herein, the phrase "substantially free of framework phosphorus," in reference to a preparation of a molecular sieve (crystalline) material, should be understood to mean that no component is added to the reaction mixture that contains more than 1.0 mol % phosphorus atoms (e.g., more than 0.5 mol % phosphorus atoms, more than 0.2 mol % phosphorus atoms, more than 0.1 mol % phosphorus atoms), based on the moles of atoms in the particular component. In addition, the phrase "substantially free of framework phosphorus," as used herein should also be understood to mean that, regardless of the components added to the reaction mixture, the framework of the molecular sieve itself contains no more than 0.2 mol % phosphorus atoms (e.g., no more than 0.1 mol % phosphorus atoms, no more than 0.05 mol % phosphorus atoms, or no more than 0.01 mol % phosphorus atoms), based on the moles of atoms in the entire molecular sieve framework. In a preferred embodiment, the molecular sieve material is completely free of framework phosphorus, i.e., contains 0 mol % phosphorus atoms.

In its calcined and anhydrous form, the CHA framework-type crystalline material of the present invention is porous and has a composition involving the molar relationship:

$$(n)X_2O_3{:}YO_2,$$

wherein X is a trivalent element, such as aluminum, boron, iron, indium, gallium or a combination thereof, typically aluminum; Y is a tetravalent element, such as silicon, tin, titanium, germanium or a combination thereof, typically silicon; and Y:X (i.e., 2/n) is from about 40 to about 60. In a preferred embodiment, the CHA framework-type aluminosilicate of the present invention is substantially free of framework phosphorus. Additionally or alternately, the aluminosilicate can advantageously exhibit an x-ray diffraction pattern having at least the following approximate peaks in Table 2:

TABLE 2

| peak d-spacing (Å) | Relative Intensities (100 I/Io) | 2Θ (degrees) (calc. as λ ≈ 1.54Å) |
|---|---|---|
| 9.08-9.15 | 60-99, such as 70-90 | 9.65-9.73 |
| 6.65-6.74 | 1-20, such as 5-15 | 13.12-13.30 |
| 6.20-6.30 | 5-25, such as 8-18 | 14.04-14.27 |

TABLE 2-continued

| peak d-spacing (Å) | Relative Intensities (100 I/Io) | 2Θ (degrees) (calc. as λ ≈ 1.54Å) |
|---|---|---|
| 5.35-5.45 | 50-80, such as 60-70 | 16.24-16.55 |
| 4.90-4.96 | 5-30, such as 13-23 | 17.86-18.08 |
| 4.18-4.25 | 80-100, such as 90-100 | 20.88-21.23 |
| 3.95-4.03 | 1-20, such as 5-15 | 22.03-22.48 |
| 3.84-3.90 | 1-20, such as 5-15 | 22.77-23.13 |
| 3.75-3.81 | 0.1-15, such as 2-10 | 23.32-23.70 |
| 3.50-3.56 | 15-45, such as 25-35 | 24.98-25.42 |
| 3.33-3.39 | 5-25, such as 10-20 | 26.26-26.74 |
| 2.84-2.90 | 1-20, such as 5-15 | 30.80-31.46 |
| 2.82-2.88 | 10-40, such as 20-30 | 31.01-31.69 |
| 2.80-2.86 | 5-25, such as 10-20 | 31.24-31.92 |
| 2.43-2.49 | 0.1-15, such as 2-10 | 36.03-36.95 |
| 2.20-2.25 | 0.1-15, such as 2-10 | 40.02-40.97 |

In one embodiment, the aluminosilicate can advantageously exhibit an x-ray diffraction pattern having at least the following peaks in Table 3:

TABLE 3

| peak d-spacing (Å) | Relative Intensities (100 I/Io) |
|---|---|
| ~9.11 | 60-99, such as 70-90 |
| ~6.69 | 1-20, such as 5-15 |
| ~6.23 | 5-25, such as 8-18 |
| ~5.40 | 50-80, such as 60-70 |
| ~4.93 | 5-30, such as 13-23 |
| ~4.21 | 80-100, such as 90-100 |
| ~3.98 | 1-20, such as 5-15 |
| ~3.87 | 1-20, such as 5-15 |
| ~3.78 | 0.1-15, such as 2-10 |
| ~3.53 | 15-45, such as 25-35 |
| ~3.36 | 5-25, such as 10-20 |
| ~2.87 | 1-20, such as 5-15 |
| ~2.85 | 10-40, such as 20-30 |
| ~2.83 | 5-25, such as 10-20 |
| ~2.46 | 0.1-15, such as 2-10 |
| ~2.22 | 0.1-15, such as 2-10 |

In its as-synthesized form, the CHA framework-type crystalline material of the present invention has a composition involving the molar relationship:

$$(n)X_2O_3{:}YO_2{:}(m)R{:}(z)H_2O,$$

wherein X, Y, and the Y:X ratio are as defined in the preceding paragraph, wherein R is at least one organic directing agent, wherein m ranges from about 0.01 to about 2, such as from about 0.1 to about 1, and wherein z ranges from about 0.5 to about 100, such as from about 2 to about 20. The R component, which is associated with the material as a result of presence during crystallization, is preferably at least partly removed by post-crystallization methods hereinafter more particularly described. Typically, the as-synthesized aluminosilicate material of the present invention contains relatively low levels of alkali metal, generally such that the combined amount of any potassium and sodium is less than 50% of the $X_2O_3$ on a molar basis. For this reason, after removal of the organic directing agent (R), the material can generally exhibit catalytic activity without a preliminary ion-exchange step to remove alkali metal cations.

To the extent desired and depending on the $X_2O_3/YO_2$ molar ratio of the material, any cations in the as-synthesized aluminosilicate material can be replaced in accordance with techniques well known in the art, at least in part, by ion exchange with other cations. Preferred replacing cations include metal ions, hydrogen ions, hydrogen precursor, e.g., ammonium ions, and mixtures thereof. Particularly preferred cations are those which tailor the catalytic activity for certain hydrocarbon conversion reactions. These include hydrogen, rare earth metals and metals of Groups IIA, IIIA, IVA, VA, IB, IIB, IIIB, IVB, VB, VIB, VIIB and VIII of the Periodic Table of the Elements.

The aluminosilicate material of the invention can be prepared from a reaction mixture containing a source of slurry medium (typically water), a source of a tetravalent element Y (typically silicon), a source of a trivalent element X (typically aluminum), and at least one organic directing agent (R) as described below. The reaction mixture is preferably substantially free of fluorine atoms and has a composition, in terms of mole ratios of oxides, within the following ranges in Table 4:

TABLE 4

| Reactants | Useful | Typical |
|---|---|---|
| $H_2O/YO_2$ | 0.1 to 20 | 2 to 10 |
| $R/YO_2$ | 0.01 to 2 | 0.1 to 1.5 |
| $X_2O_3/YO_2$ | 0 to 0.5 | 0.033 to 0.05 |

Where the tetravalent element Y is silicon, suitable sources of silicon include silicates, e.g., tetraalkyl orthosilicates, fumed silica, such as AEROSIL™ (available from Degussa), and aqueous colloidal suspensions of silica, for example that sold by E.I. du Pont de Nemours as LUDOX™. Where the trivalent element X is aluminum, suitable sources of aluminum include aluminum salts, especially water-soluble salts, such as aluminum nitrate, as well as hydrated aluminum oxides, such as boehmite and pseudoboehmite.

The organic directing agent R used herein can conveniently include a cyclic amine or ammonium compound, such as an N-substituted piperidinium compound, for example a tetraalkylpiperidinium compound, typically a N,N-diethyl-2,6-dimethyl-piperidinium compound. Suitable compounds include salts such as hydroxides.

Crystallization can be carried out at either static or stirred conditions in a suitable reactor vessel, such as for example, polypropylene jars or Teflon®-lined or stainless steel autoclaves, at a temperature from about 50° C. to about 300° C., such as from about 135° C. to about 175° C., for a time sufficient for crystallization to occur. Formation of the crystalline product can take anywhere from around 30 minutes up to as much as 2 weeks, such as from about 45 minutes to about 240 hours, for example from about 1.0 to about 120 hours. The duration can depend on many factors such as the temperature employed, with higher temperatures typically requiring shorter hydrothermal treatments.

Synthesis of the aluminosilicate may be facilitated by the presence of at least 0.1 ppm, such as at least 10 ppm, for example at least 100 ppm, conveniently at least 500 ppm of seed crystals based on total weight of the reaction mixture. The seed crystals can be homostructural with the crystalline material of the present invention, for example the product of a previous synthesis, or can be a heterostructural crystalline material, such as an LEV, CHA or OFF framework-type molecular sieve. The seeds may be added to the reaction mixture as a colloidal suspension in a liquid medium, such as water. The production of colloidal seed suspensions and their use in the synthesis of molecular sieves are disclosed, for example, in International Publication Nos. WO 00/06493 and WO 00/06494, both published on Feb. 10, 2000 and incorporated herein by reference.

Typically, the crystalline product is formed in solution and can be recovered by standard means, such as by centrifugation or filtration. The separated product can also be washed, recovered by centrifugation or filtration, and dried.

As a result of the crystallization process, the recovered crystalline product contains within its pores at least a portion of the organic directing agent used in the synthesis. Typically, therefore, the as-synthesized material is treated in manner to remove the organic directing agent from the molecular sieve, leaving active catalytic sites within the microporous channels of the molecular sieve open for contact with a feedstock. This is typically accomplished by calcining, or essentially heating the molecular sieve comprising the template at a temperature of from about 200° C. to about 800° C. in the presence of an oxygen-containing gas. In some cases, it may be desirable to heat the molecular sieve in an environment having a low or zero oxygen concentration. This type of process can be used for partial or complete removal of the organic directing agent from the intracrystalline pore system. In other cases, particularly with smaller organic directing agents, complete or partial removal from the sieve can be accomplished by conventional desorption processes.

Once the aluminosilicate material of the invention has been synthesized, it can be formulated into a catalyst composition by combination with other materials, such as binders and/or matrix materials, that provide additional hardness or catalytic activity to the finished catalyst.

Materials that can be blended with the aluminosilicate material of the invention can be various inert or catalytically active materials. These materials can include compositions such as kaolin and other clays, various forms of rare earth metals, other non-zeolite catalyst components, zeolite catalyst components, alumina or alumina sol, titania, zirconia, quartz, silica or silica sol, and mixtures thereof. These components are also effective in reducing overall catalyst cost, acting as a thermal sink to assist in heat shielding the catalyst during regeneration, densifying the catalyst and increasing catalyst strength. When blended with such components, the amount of crystalline material contained in the final catalyst product can range from 10 to 90 weight percent of the total catalyst, preferably 20 to 70 weight percent of the total catalyst.

The aluminosilicate material described herein can be used to dry gases and liquids; for selective molecular separation based on size and polar properties; as an ion-exchanger; as a chemical carrier; in gas chromatography; and as a catalyst in organic conversion reactions. Examples of suitable catalytic uses of the aluminosilicate crystalline material described herein include (a) hydrocracking of heavy petroleum residual feedstocks, cyclic stocks and other hydrocrackate charge stocks, normally in the presence of a hydrogenation component selected from Groups 6 and 8 to 10 of the Periodic Table of Elements; (b) dewaxing, including isomerization dewaxing, to selectively remove straight chain paraffins from hydrocarbon feedstocks typically boiling above 177° C., including raffinates and lubricating oil basestocks; (c) catalytic cracking of hydrocarbon feedstocks, such as naphthas, gas oils and residual oils, normally in the presence of a large pore cracking catalyst, such as zeolite Y; (d) oligomerization of straight and branched chain olefins having from about 2 to 21, preferably 2 to 5 carbon atoms, to produce medium to heavy olefins which are useful for both fuels, i.e., gasoline or a gasoline blending stock, and chemicals; (e) isomerization of olefins, particularly olefins having 4 to 6 carbon atoms, and especially normal butene to produce iso-olefins; (f) upgrading of lower alkanes, such as methane, to higher hydrocarbons, such as ethylene and benzene; (g) disproportionation of alkylaromatic hydrocarbons, such as toluene, to produce dialkylaromatic hydrocarbons, such as xylenes; (h) alkylation of aromatic hydrocarbons, such as benzene, with olefins, such as ethylene and propylene, to produce ethylbenzene and cumene; (i) isomerization of dialkylaromatic hydrocarbons, such as xylenes, (j) catalytic reduction of nitrogen oxides and (k) synthesis of monoalkylamines and dialkylamines.

In particular, the aluminosilicate material described herein can be particularly useful in the catalytic conversion of oxygenates to one or more olefins, particularly ethylene and propylene. As used herein, the term "oxygenate" is synonymous with "oxygenated hydrocarbon" and "oxygenate compound" and is defined to include, but is not necessarily limited to aliphatic alcohols, ethers, carbonyl compounds (e.g., aldehydes, ketones, carboxylic acids, carbonates, and the like), and optionally also compounds containing non-oxygen heteroatoms, such as, halides, mercaptans, sulfides, amines, and mixtures thereof. The aliphatic moiety will normally contain from about 1 to about 10 carbon atoms, such as from about 1 to about 4 carbon atoms.

Representative oxygenates include lower straight chain or branched aliphatic alcohols, their unsaturated counterparts, and their nitrogen, halogen and sulfur analogues. Examples of suitable oxygenate compounds can include, but are not limited to, methanol; ethanol; n-propanol; isopropanol; $C_4$-$C_{10}$ alcohols; methyl ethyl ether; dimethyl ether; diethyl ether; di-isopropyl ether; methyl mercaptan; methyl sulfide; methyl amine; ethyl mercaptan; di-ethyl sulfide; di-ethyl amine; ethyl chloride; formaldehyde; di-methyl carbonate; di-methyl ketone; acetic acid; n-alkyl amines, n-alkyl halides, n-alkyl sulfides having n-alkyl groups of comprising the range of from about 3 to about 10 carbon atoms; and mixtures thereof. Particularly suitable oxygenate compounds include methanol, dimethyl ether, and mixtures thereof, most preferably at least include methanol. As used herein, the term "oxygenate" designates only the reactive organic material used as the feed. The total charge of feed to the reaction zone may contain additional compounds, such as diluents.

In the present oxygenate conversion process, a feedstock comprising an organic oxygenate, optionally with one or more diluents, can be contacted in the vapor phase in a reaction zone with a catalyst comprising the molecular sieve of the present invention at effective process conditions so as to produce the desired olefins. Alternatively, the process may be carried out in a liquid or a mixed vapor/liquid phase. When the process is carried out in the liquid phase or a mixed vapor/liquid phase, different conversion rates and selectivities of feedstock-to-product may result depending upon the catalyst and the reaction conditions.

When present, the diluent(s) is(are) generally non-reactive to the feedstock or molecular sieve catalyst composition and is typically used to reduce the concentration of the oxygenate in the feedstock. Non-limiting examples of suitable diluents include, but are not limited to, helium, argon, nitrogen, carbon monoxide, carbon dioxide, water, essentially non-reactive paraffins (especially alkanes such as methane, ethane, propane, and the like), essentially non-reactive aromatic compounds, and mixtures thereof. Preferred diluents include water and/or nitrogen, with water (vapor) being particularly preferred. Diluent(s), when present, may comprise from about 1 mol % to about 99 mol % of the total feed mixture.

The temperature employed in the oxygenate conversion process may vary over a wide range, such as from about 200° C. to about 1000° C., for example from about 250° C. to about 800° C., including from about 250° C. to about 750° C., conveniently from about 300° C. to about 650° C., typically from about 350° C. to about 600° C. and particularly from about 400° C. to about 600° C.

Light olefin products will form, although not necessarily in optimum amounts, at a wide range of pressures including, but not limited to, autogenous pressures and pressures from about 0.1 kPa to about 10 MPa. Conveniently, the pressure can be from about 7 kPa to about 5 MPa, such as about 50 kPa to about 1 MPa. The foregoing pressures are exclusive of diluent, if any is present, and refer to the partial pressure of the feedstock as it relates to oxygenate compounds and/or mixtures thereof. Lower and upper extremes of pressure may adversely affect selectivity, conversion, coking rate, and/or reaction rate.

The process should be continued for a period of time sufficient to produce the desired olefin products. The reaction time may vary from tenths of seconds to a number of hours. The reaction time is largely determined by the reaction temperature, the pressure, the catalyst selected, the weight hourly space velocity, the phase (liquid or vapor) and the selected process design characteristics.

The process can be conducted at a wide range of weight hourly space velocities (WHSV) for the feedstock. WHSV is defined as weight of feed (excluding diluent) per hour per weight of a total reaction volume of molecular sieve catalyst (excluding inerts and/or fillers). The WHSV can generally be from about $0.01\ hr^{-1}$ to about $500\ hr^{-1}$, such as from about $0.5\ hr^{-1}$ to about $300\ hr^{-1}$, for example from about $0.1\ hr^{-1}$ to about $200\ hr^{-1}$.

A practical embodiment of a reactor system for the oxygenate conversion process is a circulating fluid bed reactor with continuous regeneration, similar to a modern fluid catalytic cracker. Fixed beds are generally not preferred for the process because oxygenate to olefin conversion is a highly exothermic process which requires several stages with intercoolers or other cooling devices. The reaction also results in a high pressure drop due to the production of low pressure, low density gas.

Because the catalyst must be regenerated frequently, the reactor should allow easy removal of a portion of the catalyst to a regenerator, where the catalyst is subjected to a regeneration medium, such as a gas comprising oxygen, for example air, to burn off coke from the catalyst, which restores the catalyst activity. The conditions of temperature, oxygen partial pressure, and residence time in the regenerator should be selected to achieve a coke content on regenerated catalyst of less than about 1 wt %, for example less than about 0.5 wt %. At least a portion of the regenerated catalyst should be returned to the reactor.

In one embodiment, the catalyst can be pretreated with dimethyl ether, a $C_2$-$C_4$ aldehyde composition and/or a $C_4$-$C_7$ olefin composition to form an integrated hydrocarbon co-catalyst within the porous framework of the aluminosilicate molecular sieve prior to the catalyst being used to convert oxygenate to olefins. Desirably, the pretreatment can be conducted at a temperature of at least 10° C., such as at least 25° C., for example at least 50° C., higher than the temperature used for the oxygenate reaction zone and is arranged to produce at least 0.1 wt %, such as at least 1 wt %, for example at least about 5 wt % of the integrated hydrocarbon co-catalyst, based on total weight of the molecular sieve. Such preliminary treating to increase the carbon content of the molecular sieve can also be called "pre-pooling" and is further described in U.S. Pat. Nos. 7,045,672, 7,057,083 and 7,132,581 all of which were filed Nov. 12, 2003 and are incorporated herein by reference.

In a preferred embodiment, the oxygenate conversion method comprises: (a) forming an aluminosilicate molecular sieve catalyst having a CHA framework type, which is made from a synthesis mixture comprising a silicon source, an aluminum source, a slurry medium, and a structure directing agent (template), wherein the synthesis mixture is substantially free from fluorine atoms, wherein the molecular sieve is substantially free of framework phosphorus and exhibits an x-ray diffraction pattern having at least the peaks detailed herein, and wherein the molecular sieve exhibits a Si/Al ratio from about 40 to about 60; (b) optionally formulating the molecular sieve catalyst with an oxidized aluminum-containing precursor matrix material and a clay binder to form a molecular sieve catalyst composition, wherein the composition comprises from about 20% to about 60% by weight (e.g., from about 40% to about 60% by weight) of the molecular sieve catalyst, and wherein the molecular sieve, the molecular sieve composition, or both have an attrition resistance index not greater than about 1.5 wt %/hr, e.g., not greater than about 1.2 wt %/hr, not greater than about 1.0 wt %/hr, not greater than about 0.8 wt %/hr, or not greater than about 0.5 wt %/hr (for clarity, the "optionally" at the beginning of this step means that the entire step is optional); (c) activating the molecular sieve catalyst by removing and/or decomposing the structure directing agent; and (d) contacting the activated molecular sieve catalyst with an oxygenated hydrocarbon feedstock under conditions sufficient to form an olefin product comprising ethylene and propylene in a combined amount of at least about 65%, e.g., at least about 67%, at least about 68%, at least about 69%, or at least about 70%, by weight of the olefin product, on a water-free basis, and wherein the olefin product has an ethylene-to-propylene ratio of at least about 1.2, e.g., at least about 1.3, at least about 1.35, at least about 1.4, at least about 1.45, or at least about 1.5.

In another preferred embodiment, one or more of the following are satisfied: the slurry medium comprises water; the structure directing agent preferably comprises a trialkyladamantylammonium compound, a trialkylcyclohexylammonium compound, or a combination thereof, wherein each alkyl group independently comprises from 1 to 10 carbon atoms; the synthesis mixture exhibits a water-to-silicon ratio from about 0.5 to about 100 and a structure directing agent-to-silicon ratio from about 0.01 to about 2; the olefin product comprises at least about 40% by weight of ethylene on a water-free basis; the molecular sieve catalyst and/or molecular sieve catalyst composition exhibits an on-stream lifetime of at least 7.5 (or alternately at least 8.0 or at least 8.5) grams of oxygenated hydrocarbon converted per gram of molecular sieve; and the oxygenated hydrocarbon feedstock comprises methanol, dimethyl ether, or both.

Another aspect of the invention is a process for forming an ethylene- and/or propylene-containing polymer comprising: (a) converting an oxygenated hydrocarbon feedstock into an olefin product comprising ethylene, propylene, or both, according to the oxygenate conversion method(s) described herein; (b) separating ethylene, propylene, or both from the olefin product, such that the separated ethylene and/or propylene comprises sufficiently low content(s) of conversion by-products so as to enable polymerization of the separated ethylene and/or propylene; and (c) optionally in the presence of a polymerization catalyst, and optionally in combination with one or more other comonomers and/or a diluent, polymerizing the separated ethylene and/or propylene under conditions sufficient to form an ethylene- and/or propylene-containing homopolymer, copolymer, or combination thereof (e.g., at least a polyethylene homopolymer, copolymer, or both).

While the specifications regarding the tolerable concentration of conversion by-products may vary based on various factors in the polymerization (e.g., polymerization temperature, catalyst chemistry, nature of the conversion by-products, and the like), in one embodiment, a sufficiently low content of conversion by-product(s) can be not more than about 100 ppm (e.g., not more than about 50 ppm, not more than about 20 ppm, not more than about 10 ppm, not more than about 50 ppm, not more than about 2 ppm, not more than about 1 ppm, not more than about 500 ppb, not more than about 200 ppb, not more than about 100 ppb, not more than about 50 ppb, not more than about 20 ppb, not more than about 10 ppb, or not more than about 5 ppb) by weight of the separated ethylene and/or propylene to be polymerized. Though it may be ideally desirable for there to be no detectable content of conversion by-product(s) in the separated ethylene and/or propylene, typically some detectable level will be present, e.g., at least about 0.5 ppb by weight, at least about 1 ppb by weight, or at least about 2 ppb by weight of the separated ethylene and/or propylene to be polymerized.

Another aspect of the invention relates to aluminosilicate materials having a CHA framework-type and an intermediate-to-high silica content (i.e., an Si/Al ratio greater than 24), which exhibit temperature-induced biphasic behavior above about 200° C. (e.g., from about 200° C. to about 500° C., from about 200° C. to about 450° C., from about 200° C. to about 400° C., from about 250° C. to about 500° C., from about 250° C. to about 450° C., from about 250° C. to about 400° C., from about 300° C. to about 500° C., from about 300° C. to about 450° C., or from about 300° C. to about 400° C.,), as evidenced by x-ray diffraction (XRD) analysis. For instance, CHA framework-type aluminosilicate materials having a relatively low Si/Al ratio (e.g., an Si/Al ratio of about 24 or less) show a relatively smooth decrease in one or more specific XRD peak amplitudes (e.g., for peaks centered at about 9.6 degrees 2-theta, at about 13.1 degrees 2-theta, and the like) when temperature is increased above about 200° C., whereas CHA framework-type aluminosilicate materials having an Si/Al ratio greater than about 24 show a relatively sudden and drastic decrease in one or more specific XRD peak amplitudes (e.g., for peaks centered at about 9.6 degrees 2-theta, at about 13.1 degrees 2-theta, and the like) when temperature is increased above about 200° C. This sudden and drastic peak amplitude reduction phenomenon can be accompanied by no significant/measurable change in peak area but may likely be attributable to XRD peak splitting, which indicates biphasic behavior. See, for instance, Comparative Examples 1-2 and Examples 3-5.

Additionally or alternately, the invention can further be described by the following embodiments.

Embodiment 1

A method for converting an oxygenated hydrocarbon feedstock into an olefin product comprising: (a) forming an aluminosilicate molecular sieve catalyst having a CHA framework type, which is made from a synthesis mixture comprising a silicon source, an aluminum source, a slurry medium, and a structure directing agent (template), wherein the synthesis mixture is substantially free from fluorine atoms, wherein the molecular sieve is substantially free of framework phosphorus and exhibits an x-ray diffraction pattern having at least the following peaks in Table 5:

TABLE 5

| peak d-spacing (Å) | Relative Intensities (100 I/Io) |
|---|---|
| 9.08-9.15 | 60-99 |
| 6.65-6.74 | 1-20 |

TABLE 5-continued

| peak d-spacing (Å) | Relative Intensities (100 I/Io) |
|---|---|
| 6.20-6.30 | 5-25 |
| 5.35-5.45 | 50-80 |
| 4.90-4.96 | 5-30 |
| 4.18-4.25 | 80-100 |
| 3.95-4.03 | 1-20 |
| 3.84-3.90 | 1-20 |
| 3.75-3.81 | 0.1-15 |
| 3.50-3.56 | 15-45 |
| 3.33-3.39 | 5-25 |
| 2.84-2.90 | 1-20 |
| 2.82-2.88 | 10-40 |
| 2.80-2.86 | 5-25 |
| 2.43-2.49 | 0.1-15 |
| 2.20-2.25 | 0.1-15 | and wherein the molecular sieve exhibits a Si/Al ratio from about 40 to about 60; (b) optionally formulating the molecular sieve catalyst with an oxidized aluminum-containing precursor matrix material and a clay binder to form a molecular sieve catalyst composition, wherein the composition comprises from about 20% to about 60% by weight of the molecular sieve catalyst, and wherein the molecular sieve, the molecular sieve composition, or both have an attrition resistance index not greater than about 1.5 wt %/hr; (c) activating the molecular sieve catalyst by removing and/or decomposing the structure directing agent; and (d) contacting the activated molecular sieve catalyst with an oxygenated hydrocarbon feedstock under conditions sufficient to form an olefin product comprising ethylene and propylene in a combined amount of at least about 65% by weight of the olefin product, on a water-free basis, and wherein the olefin product has an ethylene-to-propylene ratio of at least about 1.2.

Embodiment 2

The method of embodiment 1, wherein the slurry medium comprises water and wherein the structure directing agent comprises a trialkyladamantylammonium compound, a trialkylcyclohexylammonium compound, or a combination thereof, wherein each alkyl group independently comprises from 1 to 10 carbon atoms.

Embodiment 3

The method of embodiment 1 or embodiment 2, wherein the molecular sieve, the molecular sieve composition, or both have an attrition resistance index not greater than about 1.0 wt %/hr.

Embodiment 4

The method of any of the previous embodiments, wherein the olefin product comprises at least about 67% by weight of combined ethylene and propylene, on a water-free basis, wherein the olefin product has an ethylene-to-propylene ratio of at least about 1.3, or both.

Embodiment 5

The method of any of the previous embodiments, wherein the slurry medium comprises water and wherein the synthesis mixture exhibits a water-to-silicon ratio from about 0.5 to about 100 and a structure directing agent-to-silicon ratio from about 0.01 to about 2.

Embodiment 6

The method of any of the previous embodiments, wherein the olefin product comprises at least about 40% by weight of ethylene on a water-free basis.

Embodiment 7

The method of any of the previous embodiments, wherein the molecular sieve catalyst and/or molecular sieve catalyst composition exhibits an on-stream lifetime of at least 7.5 grams of oxygenated hydrocarbon converted per gram of molecular sieve.

Embodiment 8

The method of any of the previous embodiments, wherein the molecular sieve catalyst and/or molecular sieve catalyst composition exhibits an on-stream lifetime of at least 8.0 grams of oxygenated hydrocarbon converted per gram of molecular sieve.

Embodiment 9

The method of any of the previous embodiments, wherein the oxygenated hydrocarbon feedstock comprises methanol, dimethyl ether, or both.

Embodiment 10

A process for forming an ethylene- and/or propylene-containing polymer comprising: (a) converting an oxygenated hydrocarbon feedstock into an olefin product comprising ethylene, propylene, or both, according to the method of any of the previous embodiments; (b) separating ethylene, propylene, or both from the olefin product, such that the separated ethylene and/or propylene comprises sufficiently low content(s) of conversion by-products so as to enable polymerization of the separated ethylene and/or propylene; and (c) optionally in the presence of a polymerization catalyst, and optionally in combination with one or more other comonomers and/or a diluent, polymerizing the separated ethylene and/or propylene under conditions sufficient to form an ethylene- and/or propylene-containing homopolymer, copolymer, or combination thereof.

Embodiment 11

The process of embodiment 10, wherein the polymerizing step includes forming at least a polyethylene homopolymer, copolymer, or both.

EXAMPLES

In the following Examples, X-ray Powder Diffractograms (XRD spectra) were recorded on a Siemens D500 diffractometer with a voltage of about 40 kV and a current of about 30 mA, using a Cu target and Ni-filter ($\lambda \approx 0.154$ nm). Samples analyzed at room temperature (about 20-25° C.) were calcined first using the protocol set forth in Examples 14-26 below. Elemental analyses of Al, Si, and P were performed using Inductively Coupled Plasma (ICP) spectroscopy.

Thermally-programmed XRD (TP-XRD) analyses were done on a PANalytical diffractometer outfitted with an Anton Parr HTK-16 high-temperature chamber attachment, which permitted XRD spectra to be obtained with direct sample heating and in a flowing (inert) gas environment. Calcined samples were loaded onto a 20 mm L×8 mm W×0.2 mm D sample groove on a platinum heating strip. The HTK-16 chamber was sealed, and continuous $N_2$ gas flow was initiated. Samples were subject to controlled heat-up and cool-down ramping, with XRD spectra taken at each step. After a room temperature XRD, the samples were heated to about 200° C. at a rate of about 10° C./min and were held at the target temperature for about 10 minutes before an XRD analysis was initiated. The samples were then heated to about 800° C., in 50° C. increments, using the same ~10° C./min ramp rate and the same ~10 minute soak time before initiating an XRD analysis. After about 800° C., the samples were allowed to cool to about 25° C. at about −10° C./min, with a pause at about 200° C. for an XRD analysis, before a final XRD analysis after the samples had cooled to room temperature.

Comparatives Example 1-2

Comparative Example 1 involves XRD analyses of an aluminosilicate CHA framework-type material having an Si/Al ratio of about 12.5 across a variety of temperatures from about 200° C. to about 800° C. The successive TP-XRD spectra are shown graphically in FIG. 1.

Figure 2:
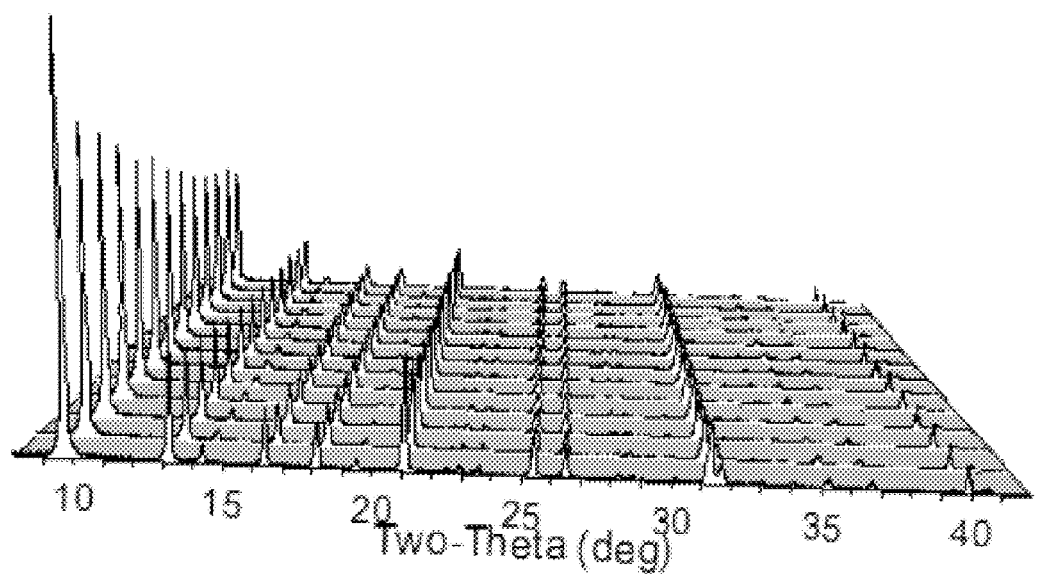
FIG. 2 shows a temperature-dependent x-ray diffraction pattern for an aluminosilicate CHA framework-type material having an Si/Al ratio of about 24.0.

Comparative Example 2 involves XRD analyses of an aluminosilicate CHA framework-type material having an Si/Al ratio of about 24.0 across a variety of temperatures from about 200° C. to about 800° C. The successive TP-XRD spectra are shown graphically in FIG. 2.

Examples 3-5

Figure 3:
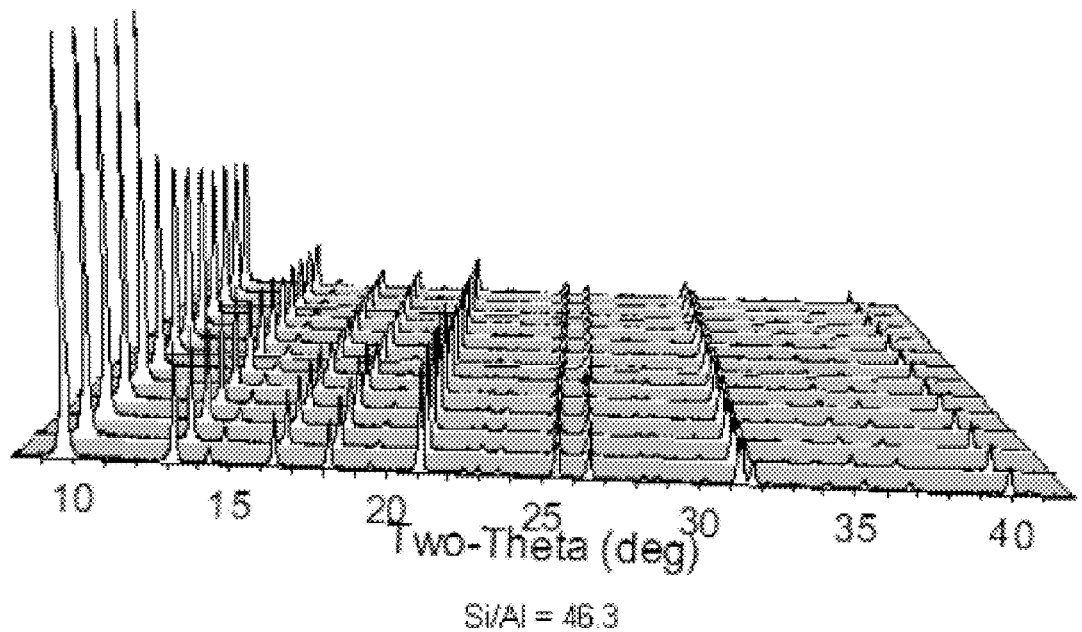
FIG. 3 shows a temperature-dependent x-ray diffraction pattern for an aluminosilicate CHA framework-type material having an Si/Al ratio of about 46.3.

Example 3 involves XRD analyses of an aluminosilicate CHA framework-type material having an Si/Al ratio of about 46.3 across a variety of temperatures from about 200° C. to about 800° C. The successive TP-XRD spectra are shown graphically in FIG. 3.

Figure 4:
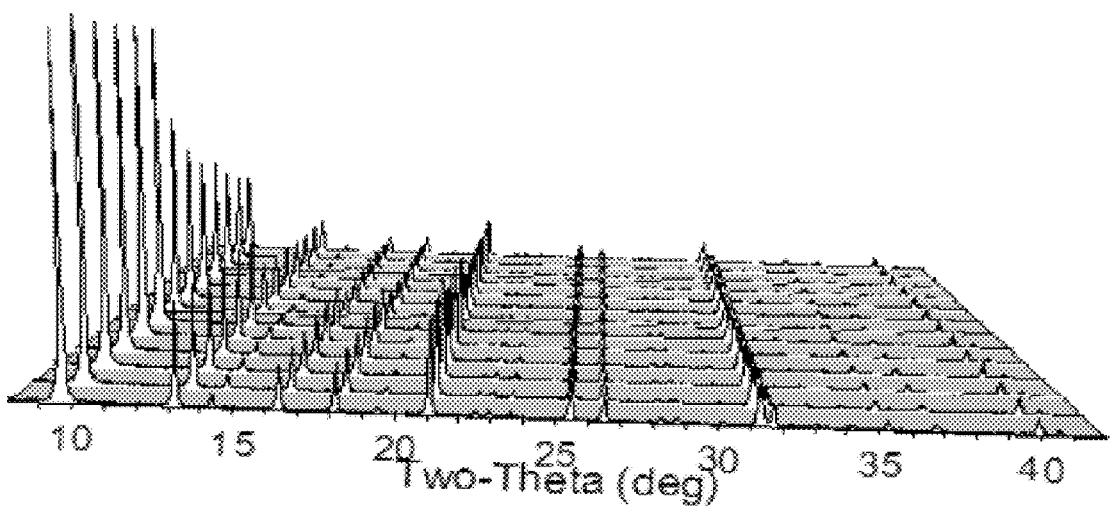
FIG. 4 shows a temperature-dependent x-ray diffraction pattern for an aluminosilicate CHA framework-type material having an Si/Al ratio of about 70.6.

Example 4 involves XRD analyses of an aluminosilicate CHA framework-type material having an Si/Al ratio of about 70.6 across a variety of temperatures from about 200° C. to about 800° C. The successive TP-XRD spectra are shown graphically in FIG. 4.

Figure 5:
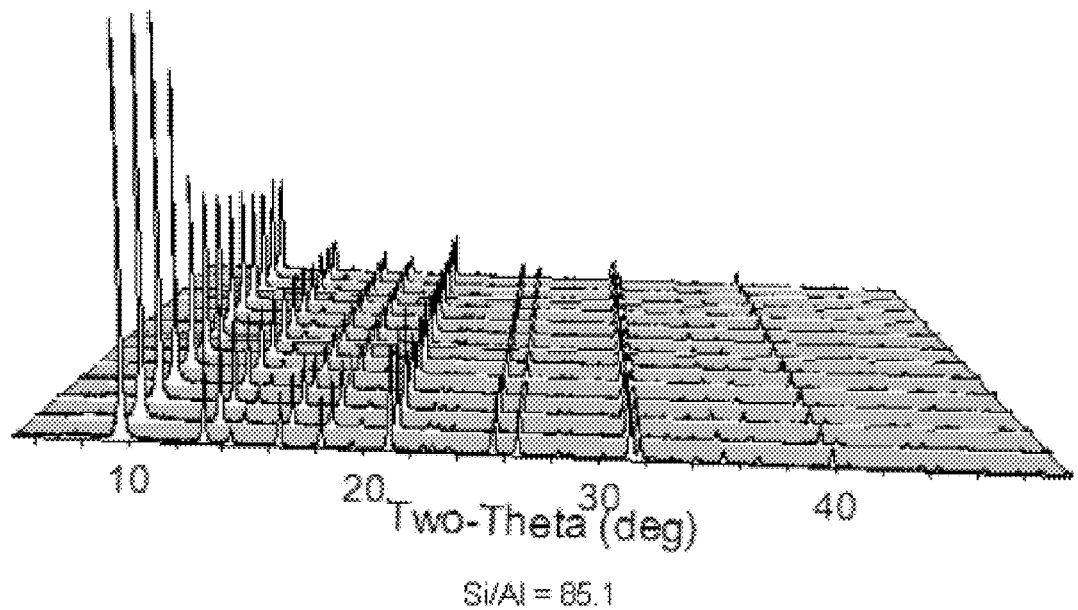
Figure 6:
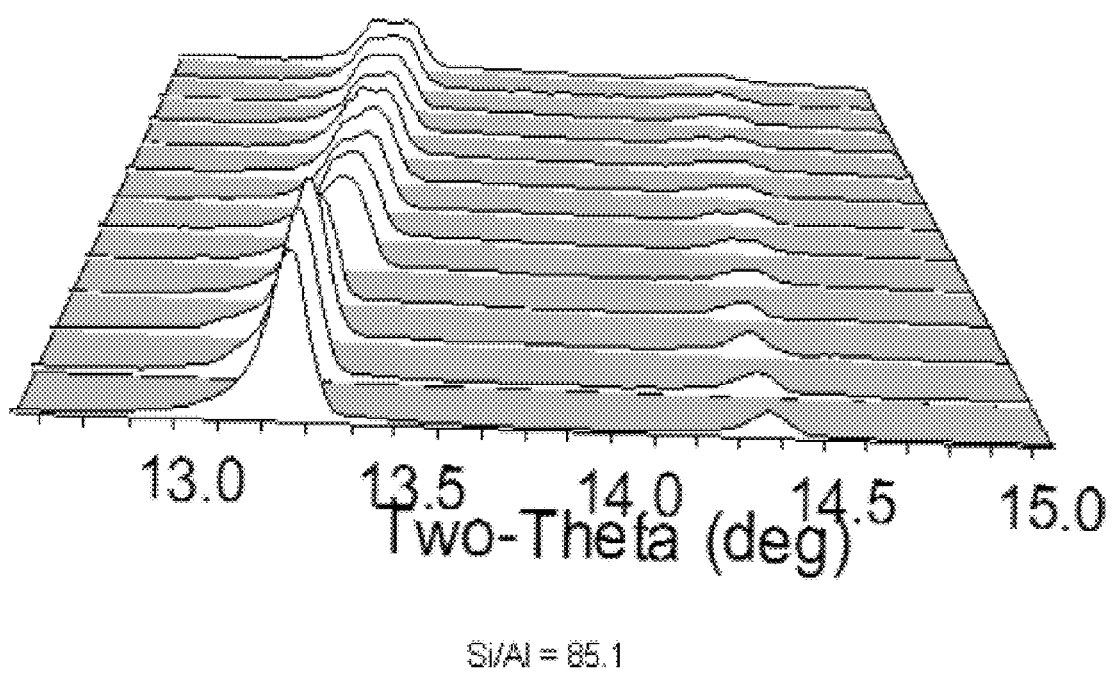
FIG. 6 shows an inset from the XRD pattern of FIG. 5.

Example 5 involves XRD analyses of an aluminosilicate CHA framework-type material having an Si/Al ratio of about 85.8 across a variety of temperatures from about 200° C. to about 800° C. The successive TP-XRD spectra are shown graphically in FIG. 5, with an inset of the region from about 12.5 to about 15.0 degrees 2-theta being shown in FIG. 6, indicating the biphasic peak-splitting and/or peak-broadening phenomenon.

Figure 7:
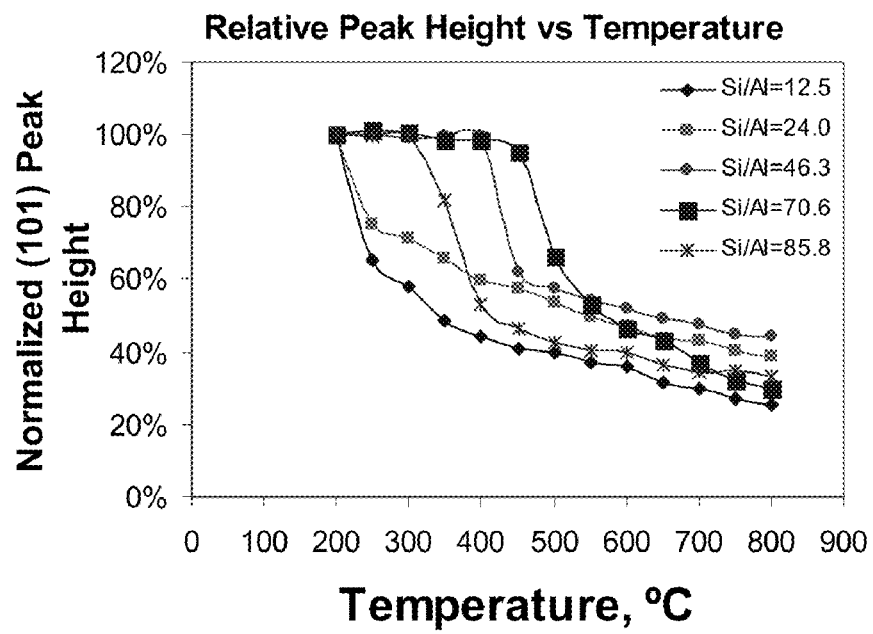
FIG. 7 shows a graph of temperature versus normalized peak height (amplitude) of the 101 peak from the x-ray diffraction patterns for the aluminosilicate CHA framework-type materials from FIGS. 1-5.

FIG. 7 shows graphically the normalized peak height (amplitude) of the 101 peak from the x-ray diffraction patterns versus temperature from about 200° C. to about 800° C. As can be seen, the abrupt change in peak height for Examples 3-5 can occur in the about 300° C. to about 500° C. temperature range, whereas no such abrupt change is observed for Comparative Examples 1-2. Thus, this biphasic behavior seems to be temperature-induced and also appeared to be reversible.

Example 6

In Example 6, the organic structure directing agent (template) N,N,N-dimethylethylcyclohexylammoniumhydroxide (DMECHA) was synthesized by the following method. About 45.0 g of ethylbromide was added to a mixture of about 50.0 g of N,N-dimethylcyclohexylamine and about 100 g of ethanol. The solution was sealed in a polypropylene bottle and was placed in a 50° C. oven overnight. The ethanol was evaporated at 50° C., with the aid of flowing nitrogen, and to the remaining thick liquid (with some crystals) was added about 50 g of deionized water. A clear solution of the bromide salt was thus obtained. The aqueous solution was ion-exchanged with Bio-Rad AG™ 1-X8 Resin (OH— exchanger) three times (3×~60 g) until $AgNO_3$ tests showed only trace amounts of silver bromide. The hydroxide solution was finally concentrated to a desired concentration by evaporating water on a Rotavap™, and the concentration was determined by titration with 0.1M HCl solution. $^{13}C$ NMR of this solution confirmed the organic purity of the template. Peaks at chemical shifts of about 70.7, about 57.6, about 46.8, about 25.0, about 24.4, about 23.9, and about 6.8 ppm were found with reference to tetramethylsilane (TMS) at 0 ppm, and relative integrated intensity ratios of 1:1:2:2:2:1:1, respectively, were observed. In this preparation, ethyliodide could replace ethylbromide for the ethylation reaction. As the iodide is more reactive, slow addition to the amine and/or chilling (e.g., with an ice bath) are recommended.

Examples 7-12

Examples 7-12 show attempts to synthesize relatively high-silica aluminosilicate materials (e.g., having an Si/Al ratio of at least about 100) using the DMECHA from Example 6 as the template material. The following ingredients were mixed, in sequence, and blended into a relatively uniform gel using a microhomogenizer (Tissue Tearor™ Model 98730, available from Biospec Products, Inc., USA): about 50 wt % NaOH in water, about 42.7 wt % N,N,N-dimethylethylcyclohexylammonium hydroxide (DMECHAOH) solution in water, deionized water (if necessary), Catapal™ A (74 wt % $Al_2O_3$, available from CONDEA Vista Company, Texas, USA), and Hi-Sil® 223 (PPG Industries, USA) which contained about 0.53 wt % Na, about 0.01 wt % K, about 0.42 wt % alumina, and about 82.2 wt % silica, where the silicon- and aluminum-containing components were added in relative amounts depending on the desired Si/Al ratio. About 200 ppm colloidal seeds (having LEV structure) were added last. The mixture was sealed in a Teflon™-lined Parr bomb with no aging and heated in an oven at a preset temperature, either statically or tumbled at about 40 rpm. After a certain time, the bomb was taken out and cooled with water to room temperature. The contents were centrifuged and washed repeatedly with deionized water. The solid product was dried in a vacuum oven at about 50° C. before a TP-XRD analysis was undertaken. The samples in the table below are ordered consecutively to be Examples 7-12 in Table 6.

TABLE 6

| Sample | | | | | | | Synthesis Condition | | | |
|---|---|---|---|---|---|---|---|---|---|---|
| | | | | | | | Agitation | Temp | Time | |
| 7 | 0.22 | HiSil233 | 1.0HiSil233 | 9.70 | 0.045 | 200 PPM | Tumbled | 170 | 3 d | ZSM-12 |
| 8 | 0.22 | HiSil233 | 1.0HiSil233 | 17.9 | 0.091 | 200 PPM | Static | 160 | 2 d | ZSM-12 |
| 9 | 0.18 | HiSil233 | 1.0HiSil233 | 6.36 | 0.127 | 200 PPM | Static | 150 | 5 d | CHA + trace ZSM-12 |
| 10 | 0.18 | HiSil233 | 1.0HiSil233 | 6.36 | 0.109 | 200 PPM | Tumbled | 150 | 3 d | CHA + trace ZSM-12 |
| 11 | 0.18 | HiSil233 | 1.0HiSil233 | 6.36 | 0.091 | 200 PPM | Tumbled | 150 | 3 d | CHA |
| 12 | 0.18 | HiSil233 | 1.0HiSil233 | 6.36 | 0.091 | 200 PPM | Tumbled | 150 | 5 d | CHA + trace ZSM-12 |

The product yield for 76-A (Example 11) was only about 11.2 wt %, on the basis of the weight of the synthesis gel. Elemental analysis revealed that the sample contained about 0.56 wt % alumina, about 72.5 wt % silica, and about 0.53 wt % Na (and below 0.01 wt % K), indicating an Si/Al ratio of about 110. These results indicate that, under certain specific but conventional synthesis conditions, relatively high-silica pure chabazite aluminosilicate materials can be synthesized in a substantially fluoride-free preparation and with a relatively low cost organic template.

Example 13

The product yield was improved when Example 11 was repeated (as Example 13), but crystallization was conducted at about 160° C. for about two days. The product was again pure chabazite, and elemental analysis demonstrated about 0.60 wt % alumina, about 76.3 wt % silica (an Si/Al ratio of about 108), about 0.33 wt % Na, and about 0.01% K. The product yield, however, was about 23.6 wt %, based on the weight of the synthesis gel. Nevertheless, crystallization at about 160° C. for times longer than about two days resulted in formation of ZSM-12 as a significant impurity.

Examples 14-26

Examples 14-26 show attempts to synthesize relatively aluminosilicate materials having a wide variety of Si/Al ratios using DMECHA as the template material in a substantially fluoride-free preparation. The following ingredients were mixed, in sequence, and blended into a relatively uniform gel using a microhomogenizer (Tissue Tearor™ Model 98730, available from Biospec Products, Inc., USA): deionized water, about 50 wt % NaOH in water, about 42.7 wt % N,N,N-dimethylethyl-cyclohexylammonium hydroxide (DMECHAOH) solution in water, Catapal™ A (74 wt % $Al_2O_3$, available from CONDEA Vista Company, Texas, USA), and Hi-Sil® 223 (PPG Industries, USA) which contained about 0.53 wt % Na, about 0.01 wt % K, about 0.42 wt % alumina, and about 82.2 wt % silica, where the silicon- and aluminum-containing components were added in relative amounts depending on the desired Si/Al ratio. About 200 ppm colloidal seeds (having LEV structure) were added last as an aqueous suspension (ppm seeds refers to weight of dry seeds with respect to weight of final gel). The gel compositions in molar ratios for these Examples were as follows: ~10 NaOH: ~20 DMECHAOH:(x) $Al_2O_3$:~110 $SiO_2$:~700$H_2O$, with "x" being variable to tune the Si/Al ratio.

The final gel mixture was sealed in a Teflon™-lined Parr bomb with no aging and heated in an oven at a preset temperature of about 160° C., which was tumbled at about 40 rpm for about 3 days (except that, for the sample having an Si/Al of about 5, the tumbling was done for about 6 days). Thereafter, the bomb was taken out and cooled with water to room temperature. In each case, a solid product was isolated by centrifugation and washed repeatedly with deionized water. Each isolated solid product was dried in a vacuum oven at about 50° C. before a TP-XRD analysis was undertaken. The table below shows the results of the aluminosilicate syntheses in Table 7.

TABLE 7

| Example | Si/Al in gel | Si/Al in product | Na/Al in product | Al per CHA cage |
|---|---|---|---|---|
| 14 | 5 | 5.13 | 0.590 | 1.958 |
| 15 | 10 | 9.78 | 0.373 | 1.113 |
| 16 | 15 | 15.8 | 0.151 | 0.714 |
| 17 | 30 | 25.5 | 0.172 | 0.453 |
| 18 | 30 | 28.6 | 0.588 | 0.405 |
| 19 | 30 | 28.8 | 0.599 | 0.403 |
| 20 | 50 | 49.6 | 0.705 | 0.237 |
| 21 | 60 | 52.0 | 0.981 | 0.226 |
| 22 | 60 | 53.3 | 0.998 | 0.221 |
| 23 | 60 | 55.3 | 0.845 | 0.213 |
| 24 | 80 | 75.3 | 1.035 | 0.157 |
| 25 | 140 | 118 | 1.977 | 0.101 |
| 26 | 164 | 120 | 2.372 | 0.099 |

In Table 7 above, the Al atoms per CHA cage were calculated assuming all Al and Si detected were T-atoms, i.e., on the CHA framework of the aluminosilicate. In this calculation, it is also given that the CHA cage is made of 12 T-atoms.

Following synthesis, the chabazite framework-type aluminosilicate molecular sieve samples of Examples 14-26 were calcined following this protocol: in flowing nitrogen, heat at a rate of about 10° C./min to about 400° C.; dwell for about 30 minutes; switch to flowing air, and resume temperature ramp at the same heating rate to about 650° C.; dwell for about 3 hours; return to about room temperature (~20-25° C.).

The calcined samples were Na ion-exchanged three times in about 5 wt % ammonium chloride solution in water. Elemental analysis (by ICP) indicated that all calcined and exchanged samples had Na/Al ratios less than about 0.03.

Following calcination, the samples of Examples 14-26 were subject to an oxygenate conversion process using methanol as the feedstock to form mainly olefin-containing carbon-based product. The methanol-to-olefins (MTO) reaction was carried out on a fixed-bed microreactor. Methanol was fed without diluent at about 100 WHSV with a vapor pressure of about 40 psia to a silica-coated stainless steel reactor tube housed in an isothermally heated zone. The reactor tube contained about 10.0 mg of granules of the calcined-and-exchanged catalyst samples (about 20-40 mesh by press-and-screen method). The catalyst samples were activated for about 30 minutes at 540° C. in flowing nitrogen before methanol was admitted. The product effluent was sampled, at different times during each run, with a twelve-port sampling loop while the catalysts were continuously deactivating (subject to oxygenate conversion conditions). Each effluent sample in each port was analyzed with a gas chromatograph (GC) equipped with an FID detector. The amount of coke on each catalyst sample at the end of the MTO test was determined on a temperature-programmed oxidation (TPO) unit. The carbonaceous material on each catalyst sample was burned off in a stream of flowing $O_2$/Ar mixture, and the CO and $CO_2$ in each effluent was converted to methane on a methanizer, which was also quantified using an FID detector.

Total conversion of methanol was expressed as cumulative methanol conversion per gram of sieve catalyst (CMCPS, total grams of MeOH converted per gram of sieve). "On-stream catalyst lifetime," as used herein, should be understood to refer to the CMCPS value when methanol conversion has dropped to about 10%. The product selectivities for each MTO sample test were reported as averages over the entire CMCPS range, rather than at any single point in the effluent composition. Complete product selectivities for all chabazite samples, including selectivity for coke, are shown in Table 8 below.

TABLE 8

| Si/Al Ratio | Al/CHA Cage | Coke wt % on Sieve by TPO | Coke Selectivity | Total g MeOH Converted, g/g | $C_2^+ + C_3^+$ (POS) | $C_2^+/C_3^+$ (POR) | $C_4^+$ | CH4 | C2α | C2o | C3α | C3o |
|---|---|---|---|---|---|---|---|---|---|---|---|---|
| 5.35 | 1.89 | 16.22 | 6.08 | 3.5 | 55.6 | 1.13 | 13.3 | 5.3 | 29.7 | 3.6 | 26.3 | 8.4 |
| 9.78 | 1.11 | 19.23 | 4.05 | 5.9 | 57.7 | 1.02 | 17.8 | 4.6 | 29.0 | 3.1 | 28.5 | 7.1 |
| 15.8 | 0.71 | 20.82 | 3.41 | 7.3 | 63.4 | 1.14 | 16.5 | 5.6 | 33.5 | 2.0 | 29.5 | 4.1 |
| 28.6 | 0.41 | no data | no data | 7.0 | 65.6 | 1.30 | 15.3 | 6.4 | 36.7 | 1.7 | 28.2 | 2.9 |
| 51.8 | 0.23 | 22.21 | 3.01 | 8.5 | 71.2 | 1.56 | 11.2 | 8.1 | 42.6 | 1.0 | 27.3 | 1.0 |
| 52.3 | 0.22 | 22.71 | 3.10 | 8.5 | 71.1 | 1.60 | 10.4 | 8.6 | 42.9 | 1.1 | 26.8 | 1.0 |
| 53.8 | 0.22 | no data | no data | 8.7 | 70.7 | 1.67 | 11.1 | 7.8 | 43.4 | 1.3 | 26.1 | 1.5 |
| 70.3 | 0.17 | 17.86 | 2.00 | 9.9 | 69.0 | 1.28 | 14.4 | 9.1 | 37.1 | 0.8 | 29.0 | 0.6 |
| 73.5 | 0.16 | 16.38 | 2.21 | 8.5 | 68.3 | 1.20 | 15.1 | 8.8 | 35.8 | 0.8 | 29.9 | 0.5 |
| 120 | 0.10 | 11.01 | 1.91 | 6.9 | 67.1 | 1.06 | 18.2 | 7.6 | 33.2 | 0.7 | 31.3 | 0.4 |
| 124 | 0.10 | 12.00 | 1.87 | 7.6 | 68.9 | 1.14 | 17.2 | 7.3 | 35.4 | 0.6 | 31.1 | 0.4 |

Figures 8A, 8B:
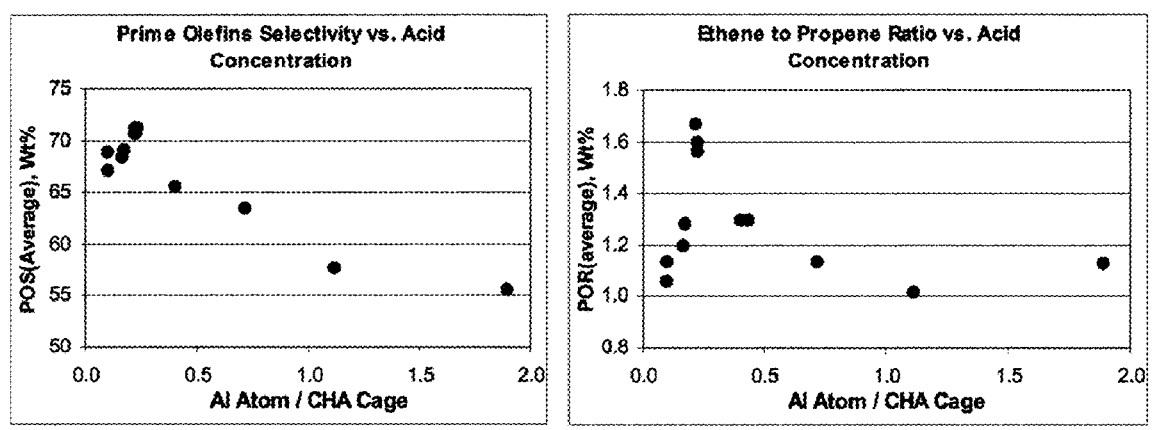
FIG. 8a graphically shows the results of MTO conversion testing of aluminosilicate CHA framework-type materials vis-à-vis a plot of the average prime olefin selectivity (POS) versus acid concentration, expressed as the average number of Al atoms per CHA cage.
FIG. 8b graphically shows the results of MTO conversion testing of aluminosilicate CHA framework-type materials vis-à-vis a plot of the average prime olefin ratio (POR) versus acid concentration, expressed as the average number of Al atoms per CHA cage.

Highlights of the MTO conversion results from Examples 14-26 can be seen graphically in FIGS. 8a and 8b, which show that both average prime olefin selectivity (POS, or the combined percent of ethylene and propylene by weight, based on the weight of the MTO product effluent, on a water-free basis) and average prime olefin ratio (POR, or ethylene-to-propylene weight ratio) have relative peaks at Si/Al ratios of about 40 to about 60 (e.g., which roughly corresponds to an average level of Al atoms per CHA cage of about 0.2 to about 0.3).

As can also be seen in FIGS. 8a-8b, the combined peaks in POS and POR occurring at the same Si/Al ratio means that ethylene selectivity (percent of ethylene by weight, based on the weight of the MTO product effluent, on a water-free basis) also peaks. The peak ethylene selectivity, about 43%, is at least as high as observed on chabazite materials based on fluoride-containing preparations.

A non-linear response in MTO performance with regard to Si/Al ratio in fluoride-free chabazite materials (SSZ-13) has been reported before (L.-T. Yuen, S. I. Zones, T. V. Harris, E. J. Gallegos, A. Auroux, *Microporous Mater.*, 1994, 2, 105), but only in the Si/Al range of 4.5 to 29. Key results are summarized in Tables 4 and 6 of the article. The aforementioned results indicate that, while total light olefin selectivity increases with increasing Si/Al ratio in that narrow range, on-stream catalyst lifetime undergoes a maximum at $Si/Al_2$ of 18. This non-monotonic response is about catalyst lifetime, and therefore is not analogous to the results disclosed herein for intermediate Si/Al ratios. The observations detailed herein have elucidated a peak in prime olefin selectivity (POS, which is defined as combined ethylene and propylene content by weight, based on the weight of the MTO effluent, on a water-free basis) at an Si/Al ratio of about 50, whereas the article reported only a monotonic selectivity increase of light olefins ($C_2$-$C_4$) only up to an Si/Al ratio of 29.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the patentable scope of the present invention.

What is claimed is:

1. A method for converting an oxygenated hydrocarbon feedstock into an olefin product comprising:
   (a) forming an aluminosilicate molecular sieve catalyst having a CHA framework type, which is made from a synthesis mixture comprising a silicon source, an aluminum source, a slurry medium, and a structure directing agent, wherein the synthesis mixture is substantially free from fluorine atoms, wherein the molecular sieve is substantially free of framework phosphorus and exhibits an x-ray diffraction pattern having at least the following peaks:

| peak d-spacing (Å) | Relative Intensities (100 I/Io) |
|---|---|
| 9.08-9.15 | 60-99 |
| 6.65-6.74 | 1-20 |
| 6.20-6.30 | 5-25 |
| 5.35-5.45 | 50-80 |
| 4.90-4.96 | 5-30 |
| 4.18-4.25 | 80-100 |
| 3.95-4.03 | 1-20 |
| 3.84-3.90 | 1-20 |
| 3.75-3.81 | 0.1-15 |
| 3.50-3.56 | 15-45 |
| 3.33-3.39 | 5-25 |
| 2.84-2.90 | 1-20 |
| 2.82-2.88 | 10-40 |
| 2.80-2.86 | 5-25 |
| 2.43-2.49 | 0.1-15 |
| 2.20-2.25 | 0.1-15 | and wherein the molecular sieve exhibits a Si/Al ratio from about 40 to about 60;
   (b) optionally formulating the molecular sieve catalyst with an oxidized aluminum-containing precursor matrix material and a clay binder to form a molecular sieve catalyst composition, wherein the composition comprises from about 20% to about 60% by weight of the molecular sieve catalyst, and wherein the molecular sieve, the molecular sieve composition, or both have an attrition resistance index not greater than about 1.5 wt %/hr;

(c) activating the molecular sieve catalyst by removing and/or decomposing the structure directing agent; and (d) contacting the activated molecular sieve catalyst with an oxygenated hydrocarbon feedstock under conditions sufficient to form an olefin product comprising ethylene and propylene in a combined amount of at least about 65% by weight of the olefin product, on a water-free basis, and wherein the olefin product has an ethylene-to-propylene ratio of at least about 1.2 by weight, based on the weight of the product from the contacting.

2. The method of claim 1, wherein the slurry medium comprises water and wherein the structure directing agent comprises a trialkyladamantylammonium compound, a trialkylcyclohexylammonium compound, or a combination thereof, wherein each alkyl group independently comprises from 1 to 10 carbon atoms.

3. The method of claim 1, wherein the molecular sieve, the molecular sieve composition, or both have an attrition resistance index not greater than about 1.0 wt %/hr.

4. The method of claim 1, wherein the olefin product comprises at least about 67% by weight of combined ethylene and propylene, on a water-free basis, or wherein the olefin product has an ethylene-to-propylene ratio of at least about 1.3, or both.

5. The method of claim 1, wherein the slurry medium comprises water and wherein the synthesis mixture exhibits a water-to-silicon ratio from about 0.5 to about 100 and a structure directing agent-to-silicon ratio from about 0.01 to about 2.

6. The method of claim 1, wherein the olefin product comprises at least about 40% by weight of ethylene on a water-free basis.

7. The method of claim 1, wherein the molecular sieve catalyst and/or molecular sieve catalyst composition exhibits an on-stream lifetime of at least 7.5 grams of oxygenated hydrocarbon converted per gram of molecular sieve.

8. The method of claim 1, wherein the molecular sieve catalyst and/or molecular sieve catalyst composition exhibits an on-stream lifetime of at least 8.0 grams of oxygenated hydrocarbon converted per gram of molecular sieve.

9. The method of claim 1, wherein the oxygenated hydrocarbon feedstock comprises methanol, dimethyl ether, or both.

10. A process for forming an ethylene- and/or propylene-containing polymer comprising:

(a) converting an oxygenated hydrocarbon feedstock into an olefin product comprising ethylene and propylene according to the method of claim 1;

(b) separating the ethylene and propylene from the olefin product, such that the separated ethylene and propylene comprises sufficiently low content(s) of conversion by-products so as to enable polymerization of the separated ethylene and/or propylene; and (c) optionally in the presence of a polymerization catalyst, and optionally in combination with one or more other comonomers and/or a diluent, polymerizing the separated ethylene and/or propylene under conditions sufficient to form an ethylene- and/or propylene-containing homopolymer, copolymer, or combination thereof.

11. The process of claim 10, wherein the polymerizing step includes forming at least a polyethylene homopolymer, copolymer, or both.

* * * * *